(12) United States Patent
Martinez et al.

(10) Patent No.: US 7,554,738 B2
(45) Date of Patent: Jun. 30, 2009

(54) OPTICAL SYSTEM WITH BEAM PROPAGATION EXTENSION

(75) Inventors: Christophe Martinez, Grenoble (FR); Christophe Kopp, Le Fontanil Cornillon (FR); Denis Pelenc, Corenc (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 11/576,845

(22) PCT Filed: Oct. 6, 2005

(86) PCT No.: PCT/FR2005/050821

§ 371 (c)(1),
(2), (4) Date: Apr. 6, 2007

(87) PCT Pub. No.: WO2006/037932

PCT Pub. Date: Apr. 13, 2006

(65) Prior Publication Data

US 2008/0088947 A1 Apr. 17, 2008

(30) Foreign Application Priority Data

Oct. 7, 2004 (FR) .................................. 04 52298

(51) Int. Cl.
*G02B 27/10* (2006.01)
*G02B 17/00* (2006.01)

(52) U.S. Cl. ...................................... 359/618; 359/726
(58) Field of Classification Search ................. 359/618, 359/625, 629, 633, 636, 637, 726, 732
See application file for complete search history.

(56) References Cited

U.S. PATENT DOCUMENTS

| 4,969,156 A | 11/1990 | Schiller et al. | |
|---|---|---|---|
| 5,303,250 A * | 4/1994 | Masuda et al. | 372/9 |
| 2002/0141697 A1 | 10/2002 | Yoon et al. | |

FOREIGN PATENT DOCUMENTS

| EP | 0 514 758 | 11/1992 |
|---|---|---|
| FR | 2 390 725 | 12/1978 |

* cited by examiner

*Primary Examiner*—Alicia M Harrington
(74) *Attorney, Agent, or Firm*—Oblon, Spivak, McClelland, Maier & Neustadt, P.C.

(57) ABSTRACT

An optical system with an optical beam propagation extension, having an input and an output for the optical beam. The system includes at least two optical reflection elements for reflection of the beam, arranged to extend the propagation of the beam by reflection on the reflection elements, and at least one optical beam transmission element arranged to be traversed at least twice by the optical beam in different directions during propagation of the optical beam in the optical system. The optical transmission element ensures an optical transformation of the optical beam each time the optical beam passes through so as to correct the divergence thereof.

12 Claims, 7 Drawing Sheets

OPTICAL SYSTEM WITH BEAM PROPAGATION EXTENSION

TECHNICAL FIELD

This invention relates to an optical system for beam propagation extension.

An optical system consists by definition of a series of optical elements through which a light beam is propagated. This invention describes the development of a system comprising a minimum number of optical elements distributed over a surface that is small but that allows for a very long beam propagation length.

This system has multiple applications, which generally satisfy two contradictory needs of integration of the component and extension of the propagation distance of the beam.

Five examples in which these two needs exist are cited below:
  the production of cavity lasers in which the spectral spacing between the emitted modes is inversely proportional and the fineness of the emission lines is directly proportional to the cavity length;
  the stabilisation of the laser diodes, which requires the use of external cavities on propagation distances much greater than the size of the component (>50 cm);
  certain interferometric applications, in which it is sometimes necessary to use delay lines to compensate for the differences in propagation between interfering beams (in particular in metrology);
  the case of mode-locking lasers in which the distribution ration is inversely proportional to the cavity length, applied to short pulse lasers;
  the case of gas sensors by absorption measurement requiring long propagation lengths in free space.

PRIOR ART

A known solution for increasing a beam propagation distance in a reduced space is to use an optical fibre. FIG. 1 shows the principle in the case of an extended cavity. In this figure, the output beam of a laser 1 is coupled to an optical fibre 2 owing to collimator optics 3. A Bragg network 4 ensures the reflection at the end of the cavity. The optical fibre is wound in a coil, allowing for a greater propagation distance between the laser and the network in a relatively reduced space. However, this solution, which is used widely today, requires the use of guided optics with coupling losses. The radius of curvature of the fibres must also be on the order of at least the centimetre, which limits integration.

Another solution, involving the production of a laser with multiple trajectories, is disclosed in document U.S. Pat. No. 6,577,666. The system disclosed implements a parabolic mirror and a series of prisms at the top so as to refocus, on the laser element, the pump beam a plurality of times. It is the reflecting element (the parabolic mirror) that performs both the reflection function and the refocusing function. Disadvantages result from this, including the complexity of the mirror and the significant bulk of the system.

The use of multiple reflections of a beam makes it possible to cause bending in the direction of propagation. The main difficulty, in the usual cavities with multiple bendings, is control of the divergence of the beam. If it is not controlled, the enlargement of the beam leads to the enlargement of the reflecting optics and consequently the increase in the volume of the system. Thus, FIG. 2 shows a first embodiment of the beam propagation. It simply involves placing mirrors 10 opposite one another, so as to bend the beam 11. For comparison, an identical beam 12 is shown without extension. If the use of the extension makes it possible to increase the distance covered by the beam with respect to a straight path (case of beam 12), it is seen that the size of the beam is also significantly increased. If the divergence of the beam is managed locally and periodically by successive systems during the propagation of the beam, the number of these systems and the size of the optics limit the compactness thereof. FIG. 3 shows a known example of the use of optics 13 for correcting the divergence of a system equivalent to that of FIG. 2. In addition to the problems of bulk associated with the size of the optics, the increase in the number of lenses considerably increases the alignment adjustment constraints.

DESCRIPTION OF THE INVENTION

This invention makes it possible to overcome the disadvantages of the prior art.

It relates to an optical system with optical beam propagation extension, having an input and an output for the optical beam, including at least two optical elements for reflection of the beam arranged to extend the propagation of the beam by reflection on the reflection elements, which optical system also includes at least one optical element for beam transmission, characterized in that the optical reflection elements have non-collinear optical axes, the optical transmission element is arranged to be traversed at least twice by said optical beam in difference directions during its propagation in the optical system, and the optical transmission element ensures an optical transformation of the beam each time it passes through so as to correct the divergence thereof.

According to an embodiment, the optical transmission element is a ball lens and the optical reflection elements are planar mirrors. In the case of a planar mirror, the optical axis is perpendicular to the plane of the mirror.

According to another embodiment, the optical transmission element is a cylindrical lens having an axis of symmetry, in which the optical elements are cylindrical mirrors with an axis of symmetry perpendicular to the axis of symmetry of the cylindrical lens. In the case of a cylindrical mirror, the optical axis is perpendicular to the axis of symmetry of the mirror.

Optionally, the optical transmission element is at least partially made of an optically active material.

Also optionally, at least one of the optical reflection elements includes an optically active material.

The optical reflection elements can be arranged to propagate the optical beam first in the reflection direction, then in the reverse direction, with the input and the output of the optical beam being coincident.

The optical system can be constituted by at least two basic optical systems arranged in cascade.

According to a particular embodiment, one of the optical reflection elements is semi-reflective so as to serve as an output for the optical beam.

The invention also relates to a gas sensor of the absorption measurement type, including an optical system with beam propagation extension as described above.

BRIEF DESCRIPTION OF THE DRAWINGS

The invention can be better understood and other advantages and special features will appear on reading the following description, given by way of a non-limiting example, accompanied by the appended drawings, in which.

DETAILED DESCRIPTION OF SPECIFIC EMBODIMENTS

The principle of the beam propagation extension system according to the invention is based on the use of transmission optics having symmetries so as to correct the divergence of the beam, and bending mirrors so as to extend the propagation distances. The symmetries of the optic enable a beam to pass through it a number of times in different directions and thus ensure the compactness of the system.

Figure 1:
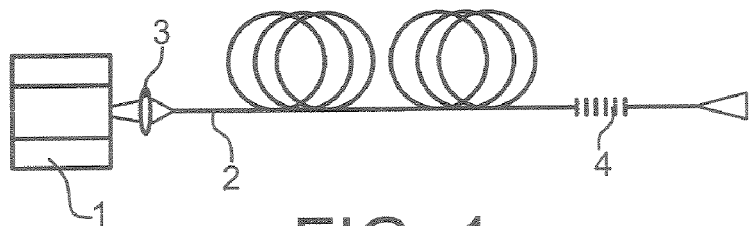
FIG. 1 shows a first optical system with beam propagation extension according to the prior art.
Figure 2:
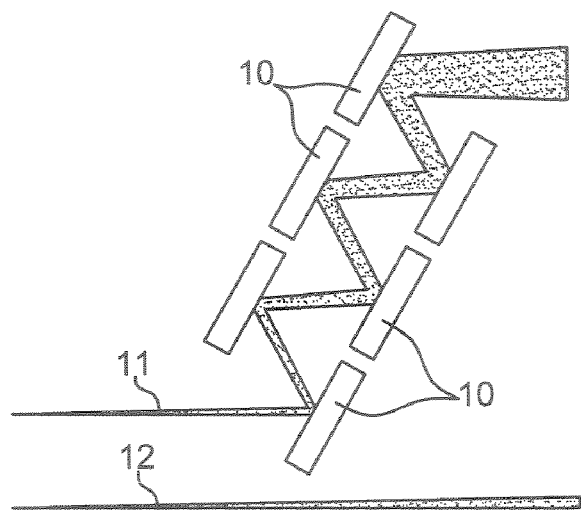
FIG. 2 shows a second optical system with beam propagation extension according to the prior art.
Figure 3:
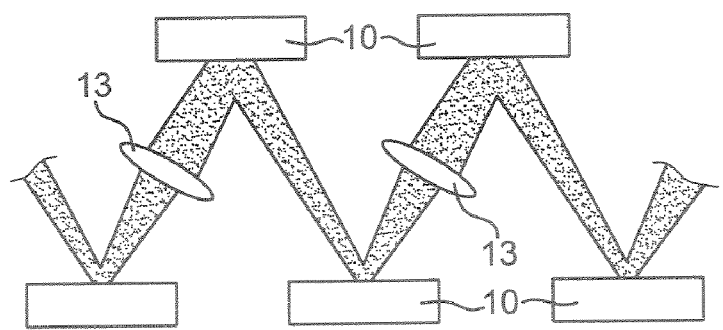
FIG. 3 shows an optical system of the type of FIG. 2 equipped with elements for correcting the divergence of the beam.
Figure 4:
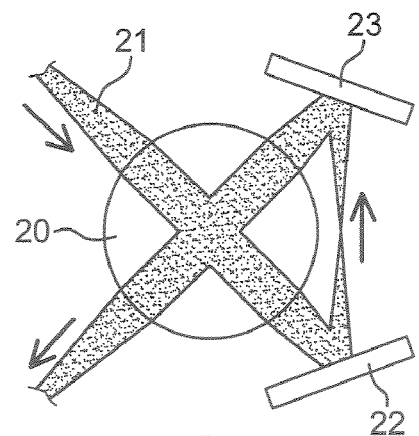
FIG. 4 shows a first alternative of the optical system according to the invention.

FIG. 4 illustrates the principle use by this invention. The optic 20 used has a circular symmetry with respect to its centre. A beam 21 first passes through the lens 20, then is reflected a first time by a first mirror 20. The mirror 22 directs the beam toward a second mirror 23, which directs the beam toward the centre of the lens 20. As it is symmetrical, the second passage of the beam is equivalent to the first. By correctly choosing the distance between the mirrors and the lens, it is thus possible to correct the divergence while increasing the beam distance covered without increasing the bulk. The optical axes of the mirrors 22 and 23 are not collinear.

Figure 5:
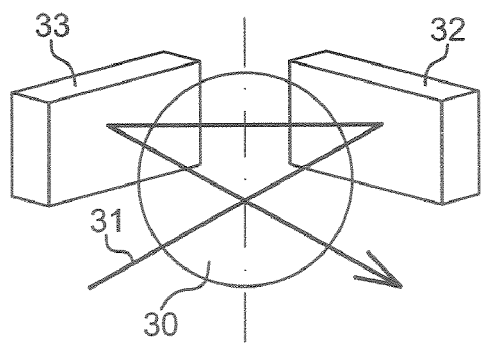
FIG. 5 shows a second alternative of the optical system according to the invention.

FIG. 5 shows a three-dimensional view of another alternative of the system according to the invention. This alternative uses two planar mirrors 32 and 33 with non-collinear optical axes and a spherical lens 30. In this case, the lens 30 alone allows for correction of the divergence of the beam 31.

Figure 6:
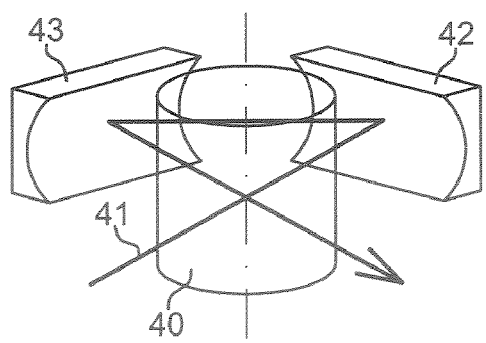
FIG. 6 shows a third alternative of the optical system according to the invention.

FIG. 6 shows a three-dimensional view of yet another alternative of the system according to the invention. This alternative uses two cylindrical mirrors 42 and 43 with non-collinear optical axes and a cylindrical lens 40. In this case, the lens 40 corrects the divergence in a first direction and the mirrors 42 and 43 correct the divergence in the other perpendicular direction while reflecting the beam 41.

Figure 7:
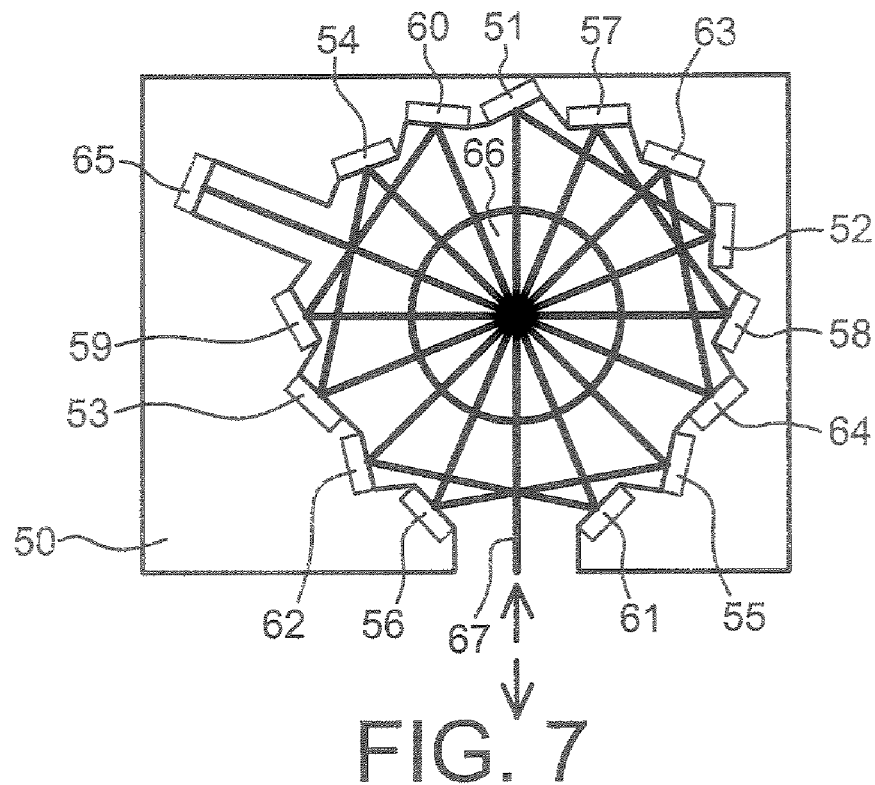
FIG. 7 shows a fourth alternative of the optical system according to the invention.

The system according to the invention becomes particularly advantageous when the number of mirrors increases. As the lens used is symmetrical, it is indeed possible to pass through it in a multitude of directions. FIG. 7 shows a system with 15 mirrors and a single lens. The system includes a part 50 having a cavity equipped with fifteen mirrors referenced 51 to 65 with non-collinear optical axes. The cavity also allows for the housing, in the central portion, of a lens (spherical or cylindrical) 66. Spherical lenses are preferred because they make it possible to correct the complete divergence of the beam (according to the two axes). A cylindrical lens, which corrects only the divergence according to one axis (that perpendicular to the axis of the lens), can be used for systems without size restrictions according to the axis of said cylinder. A light beam 67 enters the cavity as it is directed toward the mirror 51 after having passed through the lens 66. It is successively sent toward the other mirrors in ascending order of their references, passing through the lens 66 after two reflections. When the beam reaches the last mirror, mirror 65, it is reflected back on itself and repeats the path that it made previously, in the reverse direction. The beam then leaves the cavity through the place where it entered. It is easy to envisage a large propagation distance between the input and the output of the beam in spite of a reduced component surface and the use of a single optic. This example typically corresponds to the production of an extended cavity.

Figure 8:
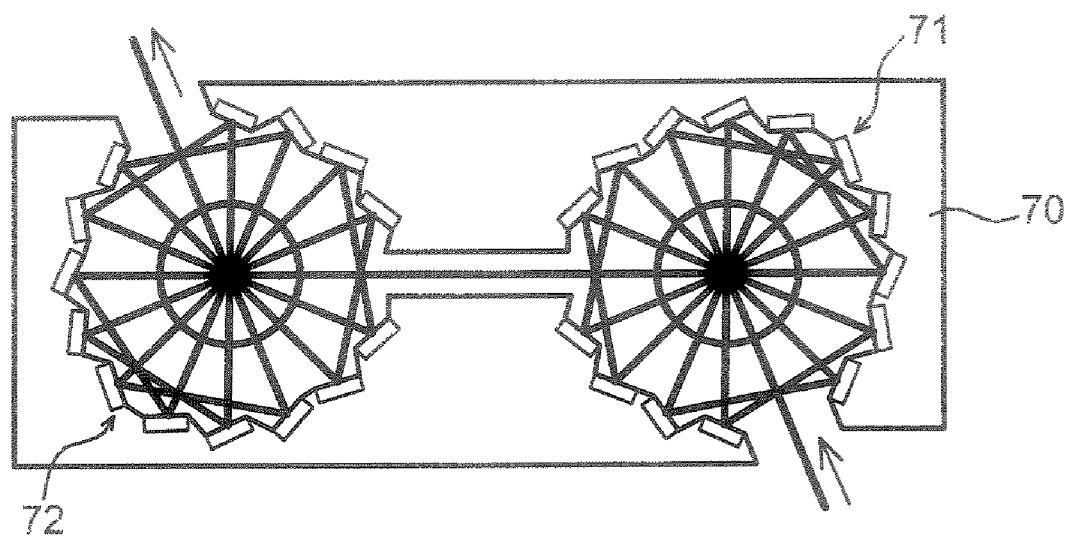
FIG. 8 shows a fifth alternative of the optical system according to the invention.

FIG. 8 shows a system including two subsystems 71 and 72 of the type of FIG. 7 arranged in cascade in a part 70. A beam 73 entering the subsystem 71 leaves said subsystem to be directed into subsystem 72 and leave the subsystem 72. The system of FIG. 8 can be used in the case of a transmission delay line.

Figure 9:
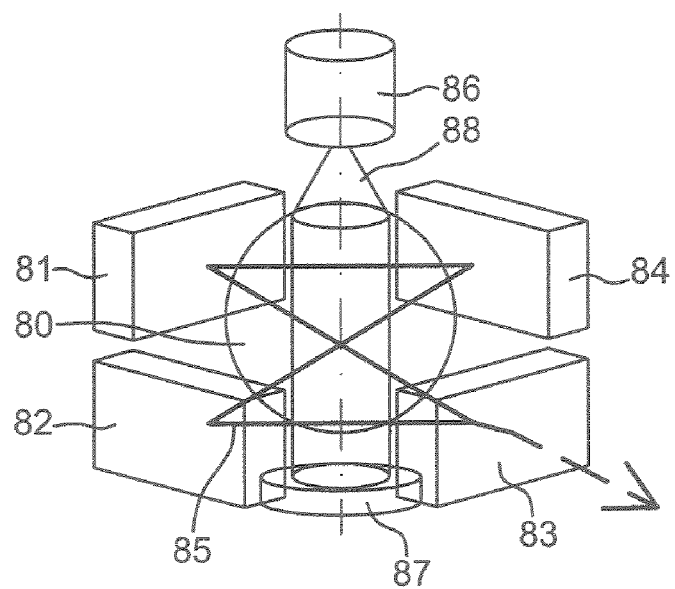
FIG. 9 shows a sixth alternative of the optical system according to the invention.

FIG. 9 shows another application of this invention. In this application, the optical transmission and divergence correction element 80 (a spherical lens) is made of an active material. By active material, we mean a material capable of transmitting an optical wave in stimulated or spontaneous transmission under the effect of a pump. The system shown includes four mirrors referenced 81 to 84 with non-collinear optical axes. This propagation extension system is closed so as to produce a stable cavity. One of the reflection elements, the mirror 83, has a lower reflection coefficient than the others so as to enable the laser beam 85 to exit. An optical source 86 serves as a pump so as to excite the active material. An additional mirror 87 makes it possible optionally to increase the confinement of the pump beam 88 in the spherical lens 80. Each time it passes through the ball lens, the beam is amplified due to the interaction of the pump beam with the active material. This solution offers the advantage of a long cavity length with a long active beam passage length, while minimizing the bulk.

Figure 10:
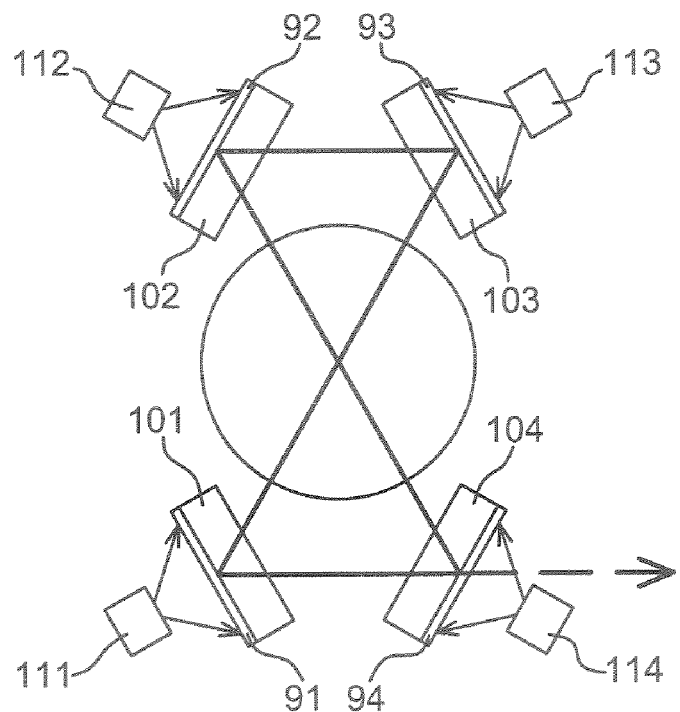
FIG. 10 shows a seventh alternative of the optical system according to the invention.

Along the same lines, it is also possible to consider a system with mirrors, comprising an area made of an active material. Such a system is shown in FIG. 10. This system is designed so that the optical wave passes through the active material before being reflected. Suitable pumping then enables the transmission in this material to be stimulated. FIG. 10 shows a system with four mirrors, including three reflecting mirrors 91, 92 and 93 and a semi-reflective mirror 94 making it possible to extract the optical wave. The mirrors 91 to 94 are covered with a layer of active material, respectively 101 to 104. The pumping of the layers of active material 101 to 104 is obtained by pump diodes, respectively 111 to 114. The mirrors 91 to 94, with non-collinear optical axes, transmit the pump beam. The beam passes through the ball lens 90 twice.

Figure 11:
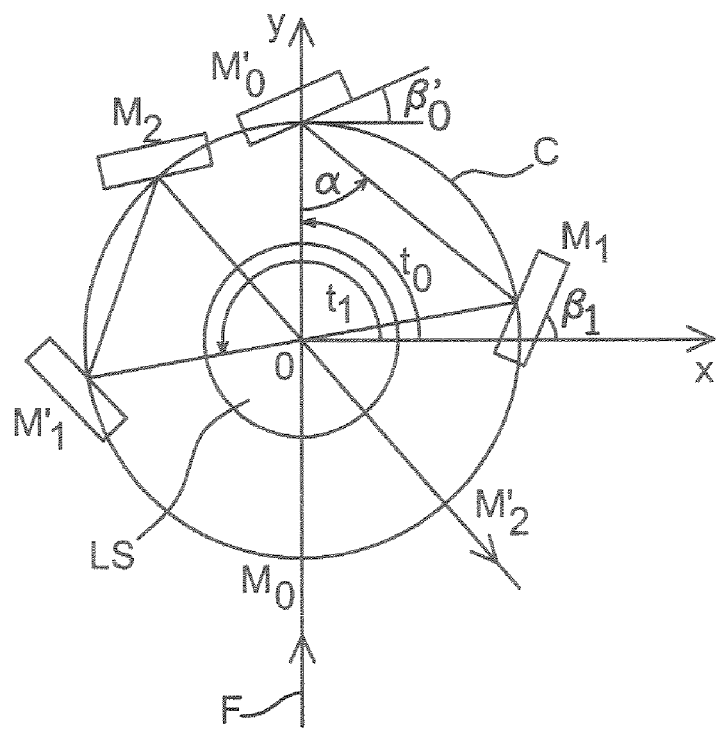
FIG. 11 shows the geometric principle of beam propagation in a system according to the invention.

FIG. 11 shows the geometric principle of propagation of the beam in a system according to the invention. The beam F is divided into primary segments $M_n M'_n$ and secondary segments $M'_n M_{n+1}$. Mirrors with non-collinear optical axes are positioned at the ends of these segments on circle C with radius R. The centre O of the circle C is the origin of the orthonormal reference x, O, y. The radius R can correspond to an incident beam with a mirror of angle α. Therefore, if $t_o$ is the angle at the origin and if $t_n$ indicates the angle of the segment $M_n M'_n$ with the axis x, the following can be written:

$$t_n = t_o + 2n\alpha \qquad (1)$$

If βn and β'n are the mirror angles at points $M_n$ and $M'_n$, then:

$$\beta_n = t_n - (\pi + \alpha)/2 \qquad (2a)$$

$$\beta'_n = t_n - (\pi - \alpha)/2 \qquad (2b)$$

The cumulative distance of the primary and secondary segments is:

$$L_{seg} = 2R(1 + |\cos(\alpha)|) \qquad (3)$$

From point $M_0$ to point $M'_N$, the distance covered is therefore:

$$L_{tot} = 2NR(1 + |\cos(\alpha)|) + 2R \qquad (4)$$

with R being the radius of the circle supporting the mirrors.

It is generally desirable to work with equidistant mirrors. This implies that for a given N, the segment $M_N M'_N$ overlaps the segment $M_0 M'_0$. We then have:

$$\alpha = (k/N) \pi/2 \text{ with } k \in Z \qquad (5)$$

The secondary segment must not cross the spherical LS. Therefore, the following geometric condition can be defined:

$$R \sin(\alpha) > R_1 \qquad (6)$$

with $R_1$ being radius of the lens LS.

The optical system according to the invention is based primarily on the use of Gaussian beams often found in integrated optics. A simple case involves the following conditions:
  first condition: the propagation distances remain equal between each passing through the lens,
  second condition: the waist (i.e. the minimum radius of the beam) is positioned in the middle of each secondary segment.

According to Gaussian optics theory, the second condition means that the distances separating the object and image waist positions at the object and image focal points are equal. Therefore, the object and image waists have the same size, and the same optics work by magnification 1.

Figure 12:
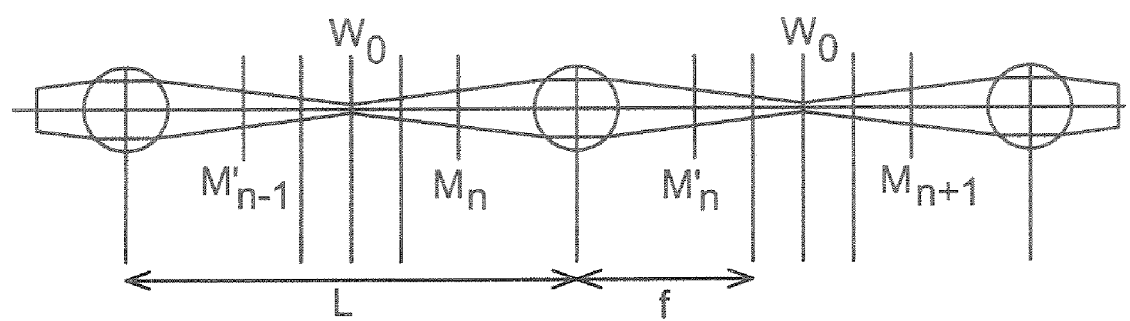
FIG. 12 is an equivalent diagram of the propagation of the unfolded system of the invention.

FIG. 12 shows an equivalent diagram of propagation of the unfolded system, in which the beam is rectilinear. The mirrors are represented by dotted lines, and the spherical lenses are represented by circles.

The lenses are separated by the distance L. It is geometrically demonstrated that:

$$L = 2R(1 + |\cos(\alpha)|) \qquad (7)$$

In addition, to satisfy the conditions of conjugation of Gaussian beams, we must have:

$$L = 2f[1 \pm ((\pi W_0^2)/(f\lambda))^2)^{0.5}] \qquad (8)$$

With Wo being the size of the waist of the beam, f being the focal length of the lens and λ being the propagation wavelength. The focal of a ball lens of index $n_1$ and the diameter $D_1$ is:

$$F = D_1 n_1 / (4(n_1 - 1)) \qquad (9)$$

It should be noted that the previous equations in condition (6) require a minimum deviation angle value of α given by the formula:

$$\alpha_{min} = \arccos((L^2 - D_1^2)/(L^2 + D_1^2)) \qquad (10)$$

Figure 13:
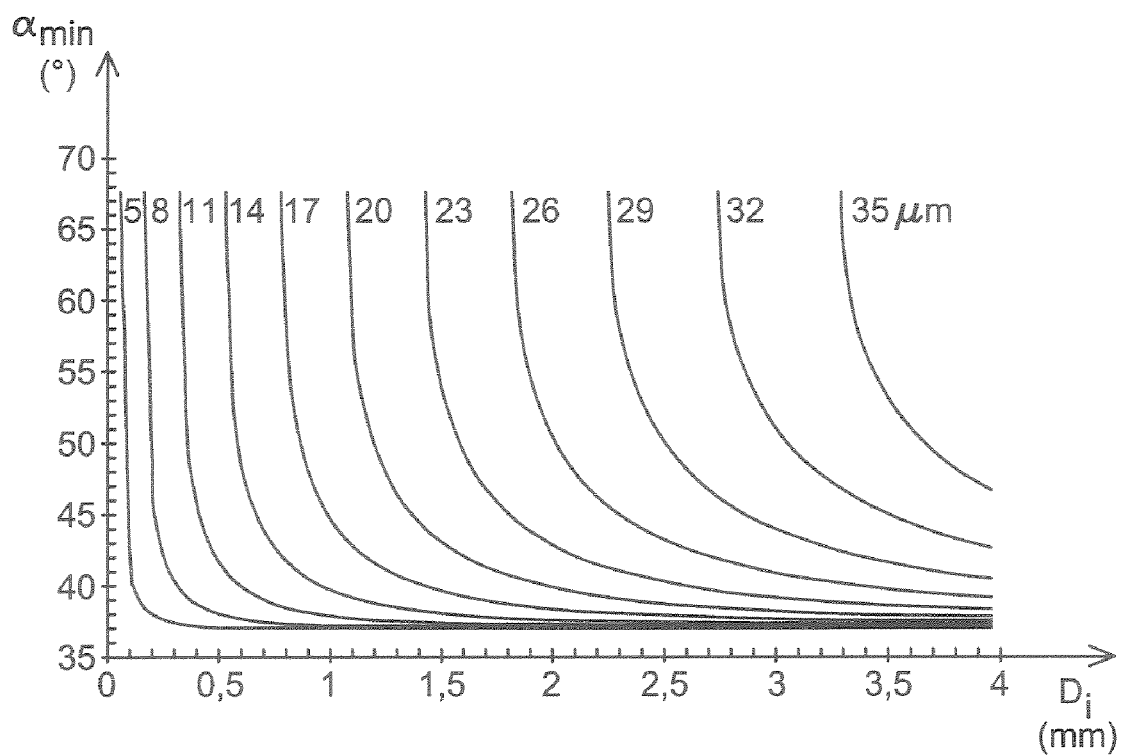
FIG. 13 is a display chart.

FIG. 13 shows the different values of minimum angles $\alpha_{min}$ according to the diameter Di of the lens for different waist sizes (the index of the glass is 1.5 and the wavelength considered is 1.55 μm).

When parameterizing the system, it is necessary to make sure that the lens does not obscure the beam. Taking into account the size of the waist, the condition (6) is expressed more precisely by the inequality:

$$R \sin(\alpha) > R_1 + W_0 \qquad (11)$$

It is also necessary for the size of the mirror to be greater than the size $2 W_M$ of the beam at its level. This size is given by the relation:

$$W_M = W_0 [1 + ((2R \cos(\alpha)\lambda)/(\pi W_0^2))^2]^{0.5} \qquad (12)$$

The size of the mirrors is associated with the angle of deviation and the diameter of the circle supporting the mirrors. The number of segments N defined in the equation (5) must therefore verify:

$$N > \pi R / (2 W_M) \qquad (13)$$

This last equation is to be calculated with the value $\alpha_{min}$ in the definition of $W_M$. It is also necessary to make sure that the tilt of the mirrors and their size does not obscure the beams reflected by neighbouring mirrors. For this, N must remain relatively low.

We will now provide an example of a possible configuration.

We will consider a ball lens with a diameter of 4 mm and a refraction index of 1.5. The propagation is produced at the wavelength 1.55 μm.

We are working with a waist of size $w_0 = 30$ μm. The equations (8), (9) and (10) give a minimum angle of deviation of 40.8°.

The equations (7), (8) and (12) give, for this minimum angle value, a mirror support radius:
$R_{min} = 3.1$ mm
and a beam radius on the mirrors of:
$W_M = 82$ μm.
The value N of the number of mirrors is limited to:
N=30.
An angle of deviation is chosen:
$\alpha = (17/30)\pi/2 = 51°$.
For this angle value, we finally have:
R=3.3 mm
L=10.76 mm
$W_M = 74.7$ mm
$L_{tot} = 32$ cm.
In this example, a surface component of less than 1 cm² allows for a propagation distance of 32 cm.

As the number of mirror reflections may be high, it is important that each angular deviation be produced with the greatest precision. Thus, in the previous configuration, an error of 0.01 degrees on the angle of the mirrors results in a shift of around 5 μm in the position of the output beam.

The embodiments of the system must therefore ensure the greatest possible angular precision. A preferred embodiment will therefore be one that implements lithographic mirrors.

Figure 14:
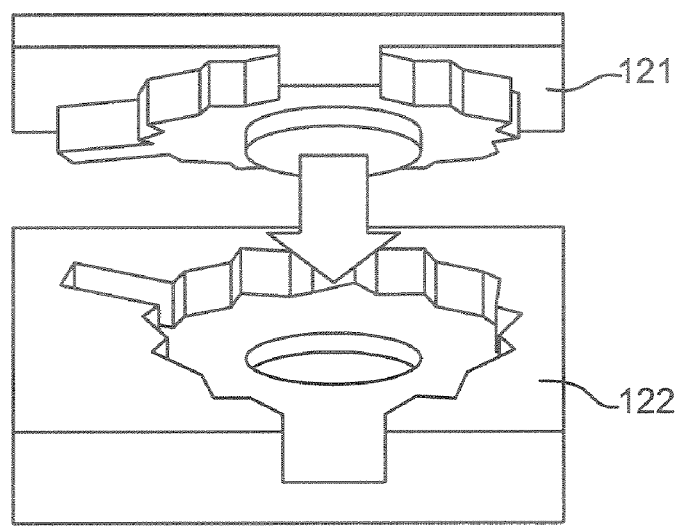
FIG. 14 shows a mode of production of the invention.

The mirrors can then be produced directly by deep etching of a substrate according to the planes of the mirrors, or by molding techniques. FIG. 14 diagrammatically shows a mould 121 and a molded substrate 122. The mould has, in the negative portion, a cavity formed by the succession of mirror planes.

Another solution involves positioning the mirrors one by one on a substrate by gluing. The positioning must then be extremely precise.

The above description relates to an optical system allowing for the propagation of a beam over a large distance generally using a single optical transmission element. To do this, said transmission element must have specific properties of symmetry, and the beam must be directed frequently by mirrors arranged appropriately.

The previous description is particularly focused on the idea of a cavity. It is possible to produce, according to the invention, an optical cavity with a long length (around 1 meter) in a very limited space (on the order of the cm$^2$). The applications of the invention therefore relate primarily to the use of cavities: lasers and interferometric sensors.

The invention has the special features of enabling, in a reduced space, a large propagation of a wave through the air (by opposition to propagation in an optical fibre in which the electromagnetic wave is confined in the silica). This structure can therefore be used for absorption sensor applications.

A typical example is the gas sensor. The presence of a gas in the atmosphere involves an increase in the absorption coefficient $\gamma$ for certain specific wavelengths, specific to the gas in question.

An optical wave propagated over a distance L will be attenuated by a factor $\rho$:

$$\rho = e^{-\gamma L} \quad (14)$$

The absorption measurement, and therefore the gas concentration, is done by measuring the factor $\rho$, the root of the ratio of the intensity of the signal transmitted $l_t$ by the intensity of the original signal $l_0$ at the characteristic wavelength:

$$\gamma = -\frac{\ln\left(\frac{l_t}{l_0}\right)}{2L} \quad (15)$$

The equation (14) shows that if $\gamma$ is very low, long propagation lengths are necessary to be capable of measuring a significant factor $\rho$.

For $\gamma \sim 0$ (with $\rho \sim 1$) it is shown that the precision of measurement is inversely proportional to L:

$$d\gamma = \frac{1}{L} d\rho \quad (16)$$

Depending on the type of gas to be detected, it is therefore important to be capable of having long propagation lengths. This need is often contradicted by the size restrictions of sensors. This invention provides a solution that satisfies both of these requirements simultaneously.

As mentioned above, the propagation length of the beam is given by the relation:

$$L_{tot} = 2NR(1+|\cos(\alpha)|) + 2R \quad (4)$$

This value also includes the propagation in the lens. To know the value of the length in the air, it is necessary to reduce the number of passages through the lens of diameter $D_1$:

$$L_{air} = 2NR(1+|\cos(\alpha)|) + 2R - ND_1 \quad (17)$$

If we take the example given above in the folded configuration (a mirror is placed at the end of the path in order to send the beam back tot he input, case of FIG. 7), we have:

$L_{tot}$=64 cm, with $D_1$=4 mm and N=30: $L_{air}$=40 cm.

We therefore have a free propagation distance of 40 cm in a structure of 1 cm$^2$.

Figure 15:
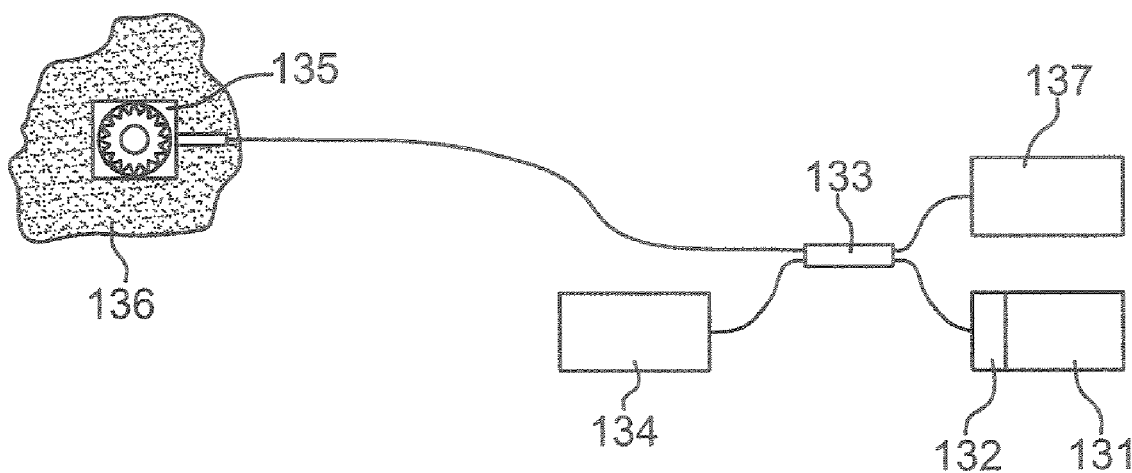
FIG. 15 shows a specific application of an optical system according to the invention.

FIG. 15 shows an example of an application of the optical system according to the invention in an absorption sensor. An optical source 131 is first filtered by a filter 132 in order to select the significant wavelength(s) and the light beam transmitted is injected into a 50/50 optical fibre coupler 133. A half of the signal is received by the optical detector 134 and serves as a reference. The other half of the signal leaves toward the sensor 135 constituted by an optical system according to the invention. The sensor 135 is placed in the gas 136 of which the absorption value is to be measured. After propagation in the optical system 135, the signal is reflected in the input fibre and, after passing through the coupler 133, is received by the detector 137. The ratio of the signals of the detectors 134 and 137 makes it possible to measure the absorption value and therefore the concentration of gas.

The invention claimed is:

1. An optical system with an optical beam propagation extension, having an input for an introduction of the optical beam and an output for an exit of the same optical beam, comprising:
   at least two optical reflection elements for reflection of the optical beam, and arranged to extend propagation of the optical beam by reflection on the optical reflection elements; and
   at least one optical transmission element for optical beam transmission,
   wherein the optical reflection elements have non-collinear optical axes,
   the optical transmission element is arranged to be traversed at least twice by the optical beam in different non-parallel directions during propagation of the optical beam in the optical system, and
   the optical transmission element ensures an optical transformation of the optical beam each time the optical beam passes through so as to correct divergence thereof.

2. An optical system according to claim 1 wherein the optical transmission element includes a ball lens and the optical reflection elements include planar mirrors.

3. An optical system according to claim 1 wherein the optical transmission element includes a cylindrical lens having an axis of symmetry, in which optical elements include cylindrical mirrors with an axis of symmetry perpendicular to an axis of symmetry of the cylindrical lens.

4. An optical system according to claim 1 wherein the optical transmission element is at least partially made of an optically active material.

5. An optical system according to claim 1 wherein at least one of the optical reflection elements includes an optically active material.

6. An optical system according to claim 1 wherein the optical reflection elements are arranged to propagate the optical beam first in a reflection direction, and then in a reverse direction, with an input and the output of the optical beam being coincident.

7. An optical system according to claim 1 wherein the optical system includes at least two basic optical systems arranged in cascade.

8. An optical system according to claim 1 wherein one of the optical reflection elements is semi-reflective so as to serve as an output for the optical beam.

9. A gas sensor of absorption measurement type, comprising:
   an optical system with beam propagation extension, wherein the optical system is an optical system according to claim 1.

10. An optical system according to claim 1 wherein said optical transmission element and said two optical reflection elements are disposed relative to each other within said optical system such that said optical beam traverses said optical transmission element during a first transmission, then after said transmission said optical beam is reflected via two consecutive reflections by said two optical reflection elements, and then after said two consecutive reflections, said optical beam traverses said optical transmission element during a second transmission.

11. An optical system according to claim 10 wherein said first and second transmissions through said optical transmission element are equal in length to each other.

12. An optical system according to claim 1 wherein said optical transmission element has a center and a circular symmetry with respect to said center.

* * * * *